(12) United States Patent
Henry

(10) Patent No.: US 6,420,383 B1
(45) Date of Patent: Jul. 16, 2002

(54) THIEPINO[3,2-B]DIHYDROPYRIDINES AND RELATED COMPOSITIONS AND METHODS

(75) Inventor: James R. Henry, Indianapolis, IN (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/802,029

(22) Filed: Mar. 8, 2001

Related U.S. Application Data

(60) Provisional application No. 60/191,659, filed on Mar. 23, 2000.

(51) Int. Cl.$^7$ .................. C07D 495/04; A61K 31/4365; A61P 11/06; A61P 37/08; A61P 13/00
(52) U.S. Cl. ........................................ 514/301; 546/114
(58) Field of Search ........................... 546/114; 514/301

(56) References Cited

U.S. PATENT DOCUMENTS

| | | | | |
|---|---|---|---|---|
| 4,285,955 A | | 8/1981 | Wehinger et al. ............ 424/266 |
| 4,483,985 A | | 11/1984 | Wehinger et al. ............ 544/131 |
| 4,532,248 A | | 7/1985 | Franckowiak et al. ...... 514/302 |
| 4,705,785 A | * | 11/1987 | Schwender et al. ......... 514/211 |
| 4,845,225 A | | 7/1989 | Schwender et al. ......... 546/114 |
| 4,879,384 A | * | 11/1989 | Schwender et al. ......... 546/114 |
| 5,075,440 A | | 12/1991 | Wustrow et al. ............ 540/468 |
| 5,708,177 A | | 1/1998 | Straub ........................ 546/267 |
| 5,756,515 A | * | 5/1998 | Urbahns et al. ............ 514/301 |

FOREIGN PATENT DOCUMENTS

| WO | WO 93/23082 | * | 11/1993 |
| WO | WO 9602547 A1 | | 2/1996 |

OTHER PUBLICATIONS

Moore, Jr. et al.; "RWJ–22108—a novel airway tissue— selective calcium channel blocker", XP–001010436, Agents Actions 40 (1993); pp. 57–61.

Dodd et al.; "Synthesis of Novel Cyclic Sulfone Dihydropyridines Facilitated by a Selective Ethyl Diazoacetate Ring Expansion"; XP–002172307, J. Heterocyclic Chem., 27, 1453 (1990); pp 1453–1456.

Dodd et al.; "Synthesis and Biological Properties of RWJ 22108, A Bronchoselective Calcium Channel Blocker", XP–002098664, Drug Design and Discovery, 1993, vol. 10; pp. 65–75.

Dodd et al.; "Design and Discovery of RWJ 22108—A novel Bronchoselective Calcium Channel Blocker"; XP–000972157, Drug Design and Discovery, 1998, vol. 15; pp. 135–148.

Pagani; "Cyclic Sulphones. Part XVIII. Probes for Conjugation of the Sulphonyl Group: Thiopyrano[3,2–b]quinoline 1,1–Dioxides"; J.C.S. Perkin II, 1974; pp. 1392–1397.

* cited by examiner

Primary Examiner—Bruck Kifle

(57) ABSTRACT

This invention provides novel thiepino[3,2-b] dihydropyridines of the following formulae:

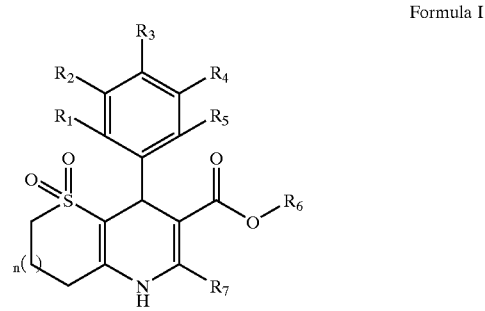

Formula I

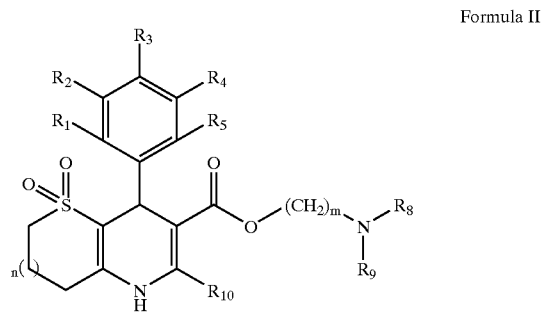

Formula II

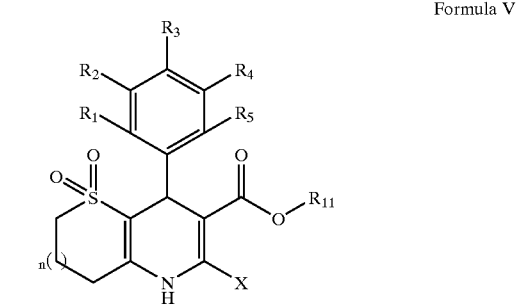

Formula V

These compounds are useful as calcium channel antagonists with cardiovascular, antiasthmatic and antibronchoconstriction activity. Thus, this invention also provides pharmaceutical compositions, as well as methods, for preventing and treating disorders such as hypersensitivity, allergy, asthma, bronchospasm, dysmenorrhea, esophageal spasm, glaucoma, premature labor, urinary tract disorders, gastrointestinal motility disorders and cardiovascular disorders.

46 Claims, No Drawings

THIEPINO[3,2-B]DIHYDROPYRIDINES AND RELATED COMPOSITIONS AND METHODS

This application claims benefit under 35 U.S.C. § 119(e) of prior application Ser. No. 60/191,659, filed Mar. 23, 2000.

FIELD OF THE INVENTION

This invention relates to novel thiepino[3,2-b] dihydropyridines useful as calcium channel blockers. These compounds, and related pharmaceutical compositions, are useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

BACKGROUND OF THE INVENTION

Thiacycloalkeno[3,2-b]pyridines are inhibitors of calcium ion uptake into smooth muscle tissue. They act to relax or prevent contraction of the tissue mediated by calcium mechanisms (Dodd et al., Drug Des. Discov. 1997 15:135–48). These compounds are active antihypertensives and bronchodilators.

Thiacycloalkeno[3,2-b]pyridines are also useful for the treatment of cardiovascular disorders, including hypertension, ischemia, angina, congestive heart failure, migraines, myocardial infarction and stroke. Such compounds are also useful for the treatment of other disorders such as hypersensitivity, allergy, asthma, dysmenorrhea, esophageal spasm, gastrointestinal motility disorders, glaucoma, premature labor and urinary tract disorders.

Dodd et al. evaluated a series of thiacycloalkeno[3,2-b] pyridines ranging in sulfone ring size from five to nine members for calcium antagonist activity. It was found that increasing the sulfone ring size from 5 to 8 members results in an in vitro potency increase of two orders of magnitude. Aromatic substitution patterns which favor tracheal effects over aortic effects were found to be 2-$NO_2$ and 2-Cl, 6-F. The ester side chain which was found to maximize in vivo activity was the N-benzyl-N-methyl aminoethyl moiety (Dodd et al., Drug Des. Discov. 1997, 15:135–48, and Drug Des. Discov. 1993, 10:65–75).

Numerous compounds related to thiacycloalkeno[3,2-b] pyridines are known, as exemplified by the following publications. U.S. Pat. No. 5,708,177 to Straub discloses a process for the preparation of optically active ortho-substituted 4-aryl- or heteroaryl-1,4-dihydropyridines by oxidation and subsequent reduction from their opposite enantiomers. U.S. Pat. No. 5,075,440 to Wustrow et al. discloses pyrido[2,3-f] [1,4]thiazepines and pyrido[3,2-b] [1,5]benzothiazepines which are useful as calcium channel antagonists with cardiovascular, antiasthmatic and antibronchoconstriction activity. U.S. Pat. Nos. 4,879,384 and 4,845, 225, both to Schwender and Dodd, disclose substituted thiacycloalkeno [3,2-b]pyridines which are also useful as calcium channel antagonists with cardiovascular, antiasthmatic and antibronchoconstrictor activity. U.S. Pat. Nos. 4,285,955 and 4,483,985 disclose acyclic sulfone substitution on simple dihydropyridines which possess calcium channel antagonist activity. U.S. Pat. No. 4,532,248 discloses a broad genus of dihydropyridines, including cyclic sulfones fused to a dihydropyridine nucleus. Cardiotonic activity is disclosed for the entire genus. However, the compounds disclosed in this patent are not taught to be calcium channel blockers. Finally, 10-Phenyl-2H-thiopyranol[3,2-b]quinolines are disclosed in Pagani, G. P. A., J. Chem. Soc. Perkin Trans. 2, 1392 (1974).

SUMMARY OF THE INVENTION

This invention provides novel thiepino[3,2-b] dihydropyridines as defined hereinbelow, as well as methods for making same. This invention also provides a pharmaceutical composition comprising the instant compound and a pharmaceutically acceptable carrier.

This invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

Finally, this invention provides an apparatus for administering to a subject the instant pharmaceutical composition, comprising a container and the pharmaceutical composition therein, whereby the container has a means for delivering to the subject a therapeutic and/or prophylactic dose of the pharmaceutical composition.

DETAILED DESCRIPTION OF THE INVENTION

This invention provides a compound of Formula I,

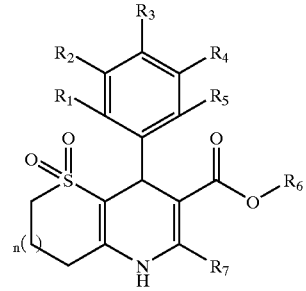

Formula I or a pharmaceutically acceptable salt thereof, wherein
(a) $R_1$, $R_2$, $R_3$, $R_4$ and $R_5$ are independently selected from H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) $R_6$ is selected from H, $C_{1-5}$ straight or branched alkyl, substituted alkyl, aryl, 3-piperidyl, N-substituted 3-piperidyl, and N-substituted 2-pyrrolidinyl methylene, wherein
said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
(i) R' and R" are independently selected from the group consisting of H, $C_{1-8}$ straight or branched alkyl, $C_{3-7}$ cycloalkyl, phenyl, benzyl, and phenethyl, or (ii) R' and R" together form a heterocyclic ring selected from the group consisting of piperidino, pyrrolidino, morpholino, thiomorpholino, piperazino, 2-thieno, 3-thieno, and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl);

(c) $R_7$ is selected from aryl, 3-pyridyl, 2-thieno, and 3-thieno; and (d) n is an integer from 1 to 5.

This invention also provides a compound of Formula II,

Formula II

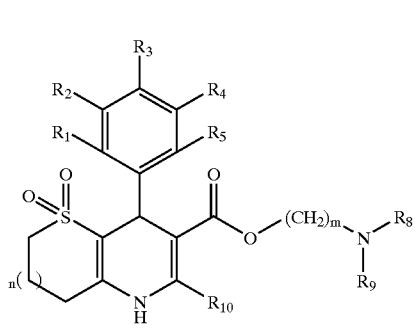

or a pharmaceutically acceptable salt thereof, wherein (a) $R_1$, $R_2$, $R_3$, $R_4$ and $R_5$ are independently selected from H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);

(b) $R_8$ is —$(CH_2)_p$(heterocyclyl) or —$(CH_2)_p$(aryl);

(c) $R_9$ is selected from H, alkyl, cycloalkyl, aryl, and arylalkyl;

(d) $R_{10}$ is selected from H, amino, alkyl, aryl, trifluoromethyl, and alkoxymethyl; and (e) m, n, and p are each an integer from 1 to 5.

The following compounds are embodiments of the present invention, wherein the compound names were produced from compound structures by ACD/INDEX NAME v.4.08, a chemical compound-naming software by Advanced Chemistry Development, Inc.:

Thiepino[3,2-b]pyridine-3-carboxylic acid, 4-(4-chlorophenyl)-1,4,6,7,8,9-hexahydro-2-phenyl-, ethyl ester, 5,5-dioxide;

Thiepino[3,2-b]pyridine-3-carboxylic acid, 4-(2,3-dichlorophenyl)-1,4,6,7,8,9-hexahydro-2-phenyl-, ethyl ester, 5,5-dioxide;

Thiepino[3,2-b]pyridine-3-carboxylic acid, 4-(3-chlorophenyl)-1,4,6,7,8,9-hexahydro-2-phenyl-, methyl ester, 5,5-dioxide;

Thiepino[3,2-b]pyridine-3-carboxylic acid, 4-(3-chlorophenyl)-1,4,6,7,8,9-hexahydro-2-phenyl-, 2-[methyl(phenylmethyl)amino]ethyl ester, 5,5-dioxide;

Thiepino[3,2-b]pyridine-3-carboxylic acid, 4-(2-chloro-6-hydroxyphenyl)-1,4,6,7,8,9-hexahydro-2-phenyl-, 2-[methyl(phenylmethyl)amino]ethyl ester, 5,5-dioxide;

Thiepino[3,2-b]pyridine-3-carboxylic acid, 4-(2-chlorophenyl)-1,4,6,7,8,9-hexahydro-2-phenyl-, 2-[methyl(phenylmethyl)amino]ethyl ester, 5,5-dioxide;

Thiepino[3,2-b]pyridine-3-carboxylic acid, 4-(2-chloro-6-hydroxyphenyl)-1,4,6,7,8,9-hexahydro-2-phenyl-, ethyl ester, 5,5-dioxide;

Thiepino[3,2-b]pyridine-3-carboxylic acid, 4-(2-chlorophenyl)-1,4,6,7,8,9-hexahydro-2-phenyl-, ethyl ester, 5,5-dioxide;

Thiepino[3,2-b]pyridine-3-carboxylic acid, 4-(2-chloro-6-fluorophenyl)-1,4,6,7,8,9-hexahydro-2-methyl-, 2-[methyl(2-thienylmethyl)amino]ethyl ester, 5,5-dioxide;

Thiepino[3,2-b]pyridine-3-carboxylic acid, 1,4,6,7,8,9-hexahydro-4-(2,3,4,5,6-pentafluorophenyl)-2-phenyl-, ethyl ester, 5,5-dioxide;

Thiepino[3,2-b]pyridine-3-carboxylic acid, 1,4,6,7,8,9-hexahydro-4-(3-nitrophenyl)-2-phenyl-, ethyl ester, 5,5-dioxide;

Thiepino[3,2-b]pyridine-3-carboxylic acid, 1,4,6,7,8,9-hexahydro-2-methyl-4-(2,3,4,5,6-pentafluorophenyl)-, 2-[methyl(2-thienylmethyl)amino]ethyl ester, 5,5-dioxide;

Thiepino[3,2-b]pyridine-3-carboxylic acid, 1,4,6,7,8,9-hexahydro-2-methyl-4-(3-nitrophenyl)-, 2-[methyl(2-thienylmethyl)amino]ethyl ester, 5,5-dioxide;

Thiepino[3,2-b]pyridine-3-carboxylic acid, 4-(2-chlorophenyl)-1,4,6,7,8,9-hexahydro-2-methyl-, 2-[methyl(2-thienylmethyl)amino]ethyl ester, 5,5-dioxide;

Thiepino[3,2-b]pyridine-3-carboxylic acid, 4-(2-chlorophenyl)-1,4,6,7,8,9-hexahydro-2-(2-thienyl)-, ethyl ester, 5,5-dioxide;

Thiepino[3,2-b]pyridine-3-carboxylic acid, 4-(3-chlorophenyl)-1,4,6,7,8,9-hexahydro-2-(2-thienyl)-, ethyl ester, 5,5-dioxide;

Thiepino[3,2-b]pyridine-3-carboxylic acid, 4-(2-chlorophenyl)-1,4,6,7,8,9-hexahydro-2-phenyl-, 2-[methyl(2-thienylmethyl)amino]ethyl ester, 5,5-dioxide;

Thiepino[3,2-b]pyridine-3-carboxylic acid, 1,4,6,7,8,9-hexahydro-4-(3-nitrophenyl)-2-phenyl-, 2-[methyl(2-thienylmethyl)amino]ethyl ester, 5,5-dioxide;

Thiepino[3,2-b]pyridine-3-carboxylic acid, 4-(3-chlorophenyl)-1,4,6,7,8,9-hexahydro-2-phenyl-, 2-[methyl(2-thienylmethyl)amino]ethyl ester, 5,5-dioxide;

Thiepino[3,2-b]pyridine-3-carboxylic acid, 1,4,6,7,8,9-hexahydro-4-(3-nitrophenyl)-2-(2-thienyl)-, ethyl ester, 5,5-dioxide;

Thiepino[3,2-b]pyridine-3-carboxylic acid, 4-(2-chlorophenyl)-1,4,6,7,8,9-hexahydro-2-(3-pyridinyl)-, ethyl ester, 5,5-dioxide;

Thiepino[3,2-b]pyridine-3-carboxylic acid, 4-(3-chlorophenyl)-1,4,6,7,8,9-hexahydro-2-(3-pyridinyl)-, ethyl ester, 5,5-dioxide;

Thiepino[3,2-b]pyridine-3-carboxylic acid, 4-[2-fluoro-3-(trifluoromethyl) phenyl]-1,4,6,7,8,9-hexahydro-2-(3-pyridinyl)-, ethyl ester, 5,5-dioxide;

Thiepino[3,2-b]pyridine-3-carboxylic acid, 4-(2-chlorophenyl)-1,4,6,7,8,9-hexahydro-2-methyl-, 2-[methyl(3-thienylmethyl)amino]ethyl ester, 5,5-dioxide;

Thiepino[3,2-b]pyridine-3-carboxylic acid, 4-(2-chloro-6-hydroxyphenyl)-1,4,6,7,8,9-hexahydro-2-methyl-, 2-[methyl(3-thienylmethyl)amino]ethyl ester, 5,5-dioxide; and Thiepino[3,2-b]pyridine-3-carboxylic acid, 1,4,6,7,8,9-hexahydro-2-methyl-4-(3-nitrophenyl)-, 2-[methyl(3-thienylmethyl)amino]ethyl ester, 5,5-dioxide.

This invention also provides soft drug analogs of the compounds of Formula I. These soft drugs are characterized by a chemically labile moiety bound to the ester group in turn bound to the dihydropyridine ring structure. The soft drugs permit the instant drugs to exert their effect locally, and to subsequently be metabolized in the blood stream, thereby reducing unwanted systemic effects (e.g. low blood pressure). Use of such soft drug analogs permits the administration of greater doses of the claimed dihydropyridine compounds without subjecting the subject to intolerable levels of unwanted systemic effects.

Specifically, this invention provides compounds of Formula V,

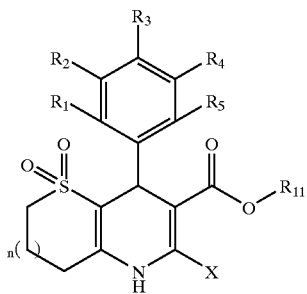

Formula V or a pharmaceutically acceptable salt thereof, wherein
(a) $R_1$, $R_2$, $R_3$, $R_4$ and $R_5$ are independently selected from H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) X is $R_7$ or $R_{10}$ wherein
$R_7$ is selected from aryl, 3-pyridyl, 2-thieno, and 3-thieno; and
$R_{10}$ is selected from H, amino, alkyl, aryl, trifluoromethyl, and alkoxymethyl;
(c) $R_{11}$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-OC(O)R''', -alkyl-C(O)R''', -alkyl-C(O)OR''', -alkyl-N(R'')C(O)R''', and -alkyl-N(R'''')C(O)OR''', wherein
R''' and R'''' are independently selected from the group consisting of hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl); and
(d) n is an integer from 1 to 5.

Each of the embodiments of the compound of Formulae I and II set forth above is also contemplated as an embodiment of the compound of Formula II. In addition, in one embodiment of Formula V, X is methyl and $R_1$, $R_2$, $R_3$, $R_4$, and $R_5$ are independently selected from hydrogen, halogen, trifluoromethyl and $NO_2$. In another embodiment of Formula V, $R_{11}$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-C(O)R''', -alkyl-N(R'')C(O)R''', and -alkyl-N(R'''')C(O)OR'''. More particularly, $R_{11}$ is selected from the group consisting of —$(CH_2)_2OC(O)CH(CH_2CH_3)_2$, —$(CH_2)_2OC(O)CH(CH_3)_2$, —$(CH_2)_2OC(O)PH$—$OCH(CH_3)_2$, —$CH_2OC(O)CH_2N(CH_3)CH_2PH$, —$CH_2OC(O)CH_2$—PH—$N(CH_3)_2$, and —$CH_2OC(O)CH(CH_2)_6$.

Unless specified otherwise, the term "alkyl" refers to a straight, branched or cyclic substituent consisting solely of carbon and H with no unsaturation. The term "alkoxy" refers to O-alkyl where alkyl is as defined. "Substituted alkyl" includes, for example, alkyl substituted with OH, halogen, cyano, $NO_2$, $C_{1-8}$ alkoxy, $C_{1-8}$ alkylsulfonyl, $C_{1-4}$ carboalkoxy, and $C_{1-8}$ alkylthio. Aryl substituents include, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ar" may be aryl or heteroaryl. Each of the terms "heterocyclyl", "heterocycle" and "heterocyclic residue" represents a single or fused ring or rings having at least one atom other than carbon as a ring member, e.g. pyridine, pyrimidine, oxazoline, pyrrole, imidazole, morpholine, furan, indole, benzofuran, pyrazole, pyrrolidine, piperidine, thiophene, and benzimidazole. Illustrative alkylamines include —$(CH_2)_2N(Me)CH_2(Ar)$, such as —$(CH_2)_2N(Me)CH_2$ (PH) and —$CH_2CH_2$—$N(Me)$—$CH_2$(heteroaryl). The symbol "Ph" or "PH" refers to phenyl. The term "halo" or "halogen" means fluoro, chloro, bromo and iodo. A "dehydrating agent," which is used in a solvent such as $CH_2Cl_2$ or toluene, includes but is not limited to sulfuric acid and acetic anhydride. "Independently" means that when there are more than one substituent, the substitutents may be different.

The compounds of the instant invention are asymmetric in the dihydropyridine ring at the 4-position and thus exist as optical antipodes. As such, all possible optical isomers, antipodes, enantiomers, and diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle type column.

As used herein, the phrase "pharmaceutically acceptable salt" means a salt of the free base which possesses the desired pharmacological activity of the free base and which is neither biologically nor otherwise undesirable. These salts may be derived from inorganic or organic acids. Examples of inorganic acids are hydrochloric acid, nitric acid, hydrobromic acid, sulfuric acid, and phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like.

The instant compounds can be prepared using readily available starting materials and reaction steps well known in the art (Edema et al. J. Org. Chem. 58: 5624–7, 1993; Howard et al., J. Amer. Chem. Soc. 82:158–64, 1960).

This invention also provides a pharmaceutical composition comprising the instant compound and a pharmaceutically acceptable carrier.

Pharmaceutical compositions containing a compound of the present invention as the active ingredient in intimate admixture with a pharmaceutical carrier can be prepared according to conventional pharmaceutical techniques. The carrier may take a wide variety of forms depending on the form of preparation desired for administration, such as systemic administration including but not limited to intravenous, oral, nasal or parenteral. In preparing the compositions in oral dosage form, any of the usual pharmaceutical carriers may be employed, such as water, glycols, oils, alcohols, flavoring agents, preservatives, coloring agents, syrup and the like in the case of oral liquid preparations (for example, suspensions, elixirs and solutions), and carriers such as starches, sugars, diluents, granulating agents, lubricants, binders, disintegrating agents and the like in the case of oral solid preparations (for example, powders, capsules and tablets).

In one embodiment, the compounds of the instant invention are administered by inhalation. For inhalation administration, the compounds can be in a solution intended for administration by metered dose inhalers, or in a form intended for a dry powder inhaler or insufflator. More particularly, the instant compounds can be conveniently delivered in the form of an aerosol spray from a pressurized container, a pack or a nebuliser with the use of a suitable propellant, e.g., dichlorodifluoromethane, trichlorofluoromethane, dichlorotetrafluoroethane, carbon dioxide or other suitable gas. The dosage unit may be determined by providing a valve to deliver a metered amount. Capsules and cartridges made of a pharmaceutically acceptable material such as gelatin for use in an inhaler or insufflator can be formulated to contain a powder mix of the compound and a suitable powder base such as lactose or starch.

Because of their ease of administration, tablets and capsules represent an advantageous oral dosage unit form wherein solid pharmaceutical carriers are employed. If desired, tablets can be sugar-coated or enteric-coated by standard techniques. For parenterals, the carrier will usually comprise sterile water, though other ingredients to aid solubility or to act as preservatives can be included. Injectable suspensions can also be prepared, wherein appropriate liquid carriers, suspending agents and the like are employed. The instant compounds can also be administered in the form of an aerosol, as discussed above.

The instant pharmaceutical composition can contain per dosage unit (e.g., tablet, capsule, powder, injection, teaspoonful and the like) from about 0.001 to about 100 mg/kg, and preferably from about 0.01 to about 20 mg/kg of the instant compound.

The compounds of the present invention inhibit the uptake of calcium ions into smooth muscle cells, and therefore act to relax or prevent calcium ion-mediated contraction of smooth muscle tissue.

Thus, this invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition. By way of example, in a subject suffering from asthma, the subject's airways are constricted due to inflammation of airway smooth muscle cells ("SMC's"). Reducing the calcium influx into the SMC's, whose action (i.e., inflammation) contributes to the disorder, would be expected to alleviate the disorder.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

In one embodiment, the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder. In the preferred embodiment, the disorder is asthma. The cardiovascular disorder can be, for example, hypertension, ischemia, angina, congestive heart failure, myocardial infarction or stroke.

As used herein, "treating" a disorder means eliminating or otherwise ameliorating the cause and/or effects thereof. "Inhibiting" the onset of a disorder means preventing, delaying or reducing the likelihood of such onset.

The term "subject" includes, without limitation, any animal or artificially modified animal. In the preferred embodiment, the subject is a human.

Methods are known in the art for determining therapeutically and prophylactically effective doses for the instant pharmaceutical composition. The effective dose for administering the pharmaceutical composition to a human, for example, can be determined mathematically from the results of animal studies.

This invention further provides an apparatus for administering to a subject the instant pharmaceutical composition, comprising a container and the pharmaceutical composition therein, whereby the container has a means for delivering to the subject a therapeutic and/or prophylactic dose of the pharmaceutical composition. In the preferred embodiment, the apparatus is an aerosol spray device for treating and/or preventing asthma via topical respiratory administration.

Finally, this invention provides processes for preparing the compound of Formula III,

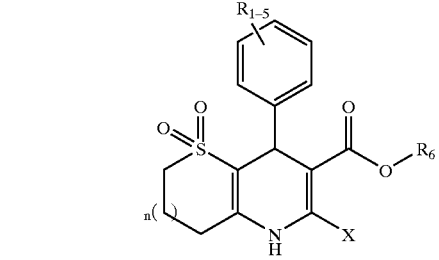

III wherein X is $R_7$ or $R_{10}$, and $R_1$, $R_2$, $R_3$, $R_4$, $R_5$, $R_6$, $R_7$, and $R_{10}$ are as set forth hereinabove.

One process of the present invention comprises the steps of:

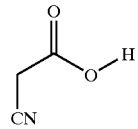
1a

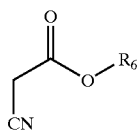
1b

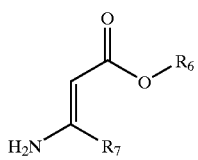
1c a) reacting a compound of Formula 1a with $HOR_6$ to form a compound of Formula 1b;

b) reacting the compound of Formula 1b with $R_7MgBr$ to form a compound of Formula 1c; and

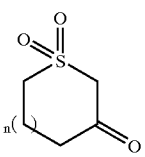
1d

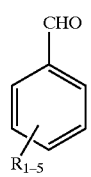
1e

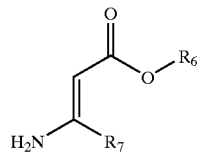
1c c) reacting a compound of Formula 1d and a compound of Formula 1e with the compound of Formula 1c to form a compound of Formula III.

Another process of the present invention comprises the step of reacting a compound of Formula 1d and a compound of Formula 1e with the compound of Formula 1f to form a compound of Formula III.

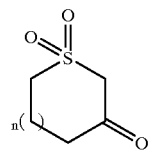
1d

1e

1f

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXPERIMENTAL DETAILS

A. Schemes and Syntheses

The compounds of Formula I can be made in accordance with the following general procedures outlined in Scheme I (Howe, R. K. et al. *J. Het. Chem.* 1978, 15, 1001; Takahashi et al. WO 98/39300; Kobayashi, T. et al. *Chem. Pharm. Bull.* 1995, 43, 797.):

Scheme I

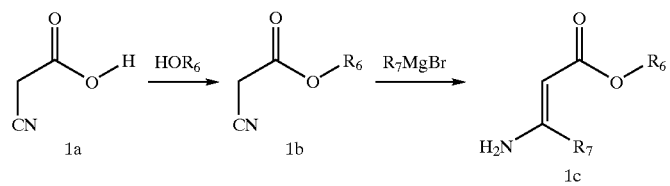

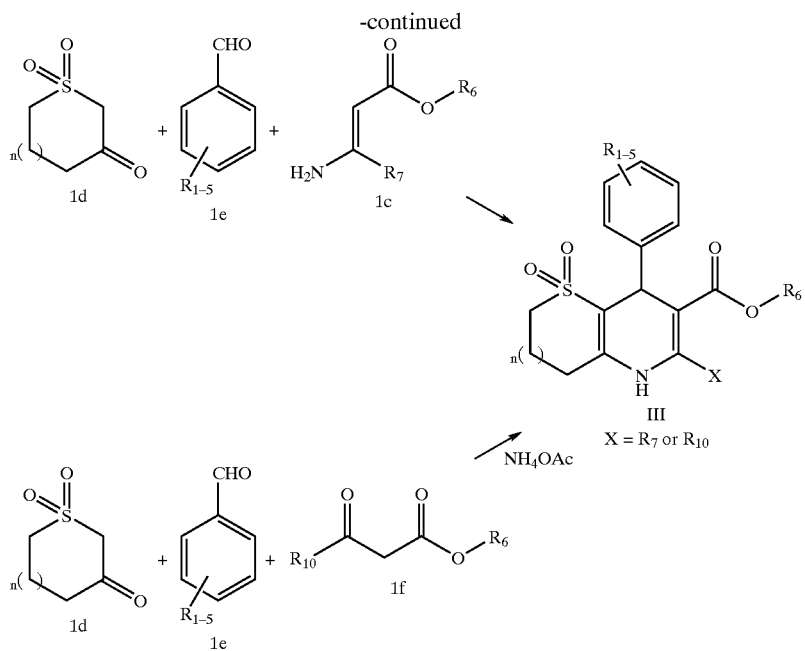

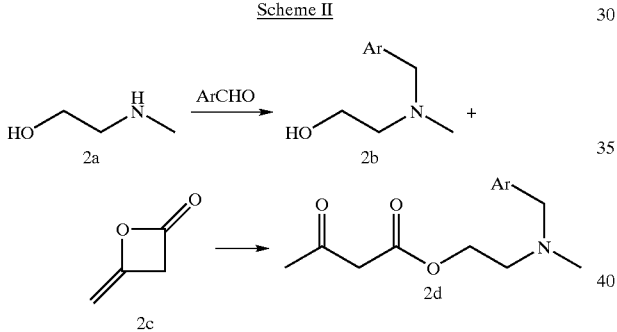

When $R_6$ is —$(CH_2)_2N(Me)CH_2(Ar)$ and $R_{10}$ is $CH_3$, compounds of Formula 1f may be made following Scheme II:

Scheme II

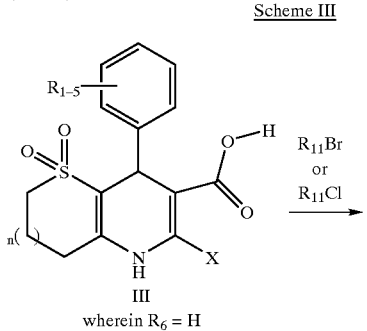

Procedures for making dihydropyrides are well documented in the art as shown in Eistert et al. (Chem. Ber. 110, 1069–1085,1977), G. A. Pagani (J. Chem. Soc., Perkin Trans. 2, 1392–7,1974), Mason et al. (J. Chem. Soc. (C) 2171–76, 1967), E. A. Fehnel (J. Amer. Chem. Soc. 74,1569–74, 1952), and M. Seiyaku (Japan Patent Application No. 58201764, 1984).

The compounds of Formula V can be made in accordance with Scheme III, wherein X, n, $R_{1-7}$ and $R_{10-11}$ are as described above, preferably in the presence of $K_2CO_3$ or $CsCO_3$ in an organic solvent such as dimethylformamide (DMF).

Scheme III

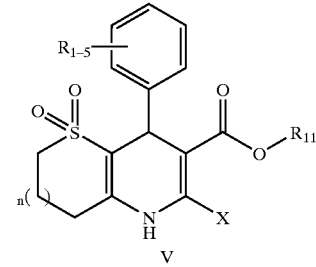

-continued

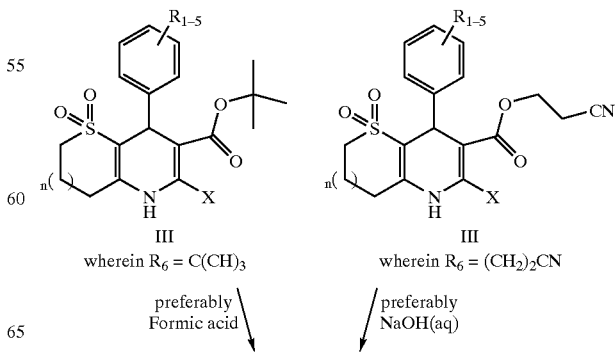

The compounds of Formula V may also be made in accordance with Scheme IV, wherein X, n, $R_{1-7}$ and $R_{10-11}$ are as described above, preferably in the presence of formic acid or NaOH (aq), respectively.

Scheme IV

-continued

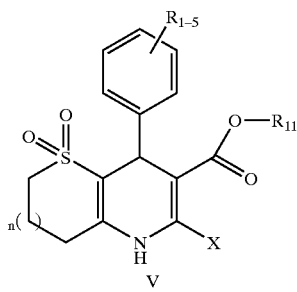

V

The Examples below describe in greater detail the chemical syntheses of representative compounds of the present invention. The rest of the compounds disclosed herein can be prepared similarly in accordance with one or more of these methods. No attempt has been made to optimize the yields obtained in these syntheses, and it would be clear to one skilled in the art that variations in reaction times, temperatures, solvents, and/or reagents could be used to increase such yields.

Table 1 below sets forth the mass spectra data, the inhibition of nitrendipine binding and inhibition of calcium-dependent smooth muscle contraction for the instant compounds tested.

TABLE 1

Molecular Weight, Mass Spectra Data and
Calcium Channel Antagonist Activity for Compounds 1–26

Formula IV

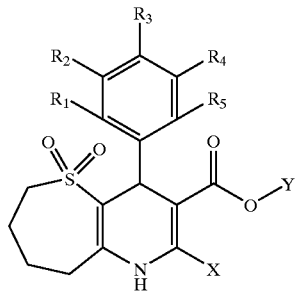

| Compound No. | $R_1$ | $R_2$ | $R_3$ | $R_4$ | $R_5$ | Y | X | Mol. Wt. | $IC_{50}$ nM |
|---|---|---|---|---|---|---|---|---|---|
| 1 | H | H | Cl | H | H | Et | Ph | 457.9756 | 2000 |
| 2 | H | H | H | Cl | Cl | Et | Ph | 492.4207 | 115 |
| 3 | H | H | H | Cl | H | Me | Ph | 443.9488 | 2000 |
| 4 | H | H | H | Cl | H | $CH_2CH_2N(CH_3)CH_2Ph$ | Ph | 577.1417 | 192 |
| 5 | Cl | H | H | H | OH | $CH_2CH_2N(CH_3)CH_2Ph$ | Ph | 593.1407 | 2000 |
| 6 | H | H | H | H | Cl | $CH_2CH_2N(CH_3)CH_2Ph$ | Ph | 577.1417 | 312 |
| 7 | Cl | H | H | H | OH | Et | Ph | 473.9746 | 2000 |
| 8 | H | H | H | H | Cl | Et | Ph | 457.9756 | 580 |
| 9 | Cl | H | H | H | F | $CH_2CH_2N(CH_3)CH_2$-2-thiophene | Me | 539.0892 | 29.5 |
| 10 | F | F | F | F | F | Et | Ph | 513.481 | 684 |
| 11 | H | H | H | $NO_2$ | H | Et | Ph | 468.5276 | 6950 |
| 12 | F | F | F | F | F | $CH_2CH_2N(CH_3)CH_2$-2-thiophene | Me | 576.6046 | 5.9 |
| 13 | H | H | H | $NO_2$ | H | $CH_2CH_2N(CH_3)CH_2$-2-thiophene | Me | 531.6511 | 7.1 |
| 14 | H | H | H | H | Cl | $CH_2CH_2N(CH_3)CH_2$-2-thiophene | Me | 521.0991 | 15 |
| 15 | H | H | H | H | Cl | Et | 2-Thienyl | 464.0038 | 2500 |
| 16 | H | H | H | Cl | H | Et | 2-Thienyl | 464.0038 | 2300 |
| 17 | H | H | H | H | Cl | $CH_2CH_2N(CH_3)CH_2$-2-thiophene | Ph | 583.1699 | 500 |
| 18 | H | H | H | $NO_2$ | H | $CH_2CH_2N(CH_3)CH_2$-2-thiophene | Ph | 593.7219 | 26000 |
| 19 | H | H | H | Cl | H | $CH_2CH_2N(CH_3)CH_2$-2-thiophene | Ph | 583.1699 | 1289 |
| 20 | H | H | H | $NO_2$ | H | Et | 2-Thienyl | 474.5558 | 6544 |
| 21 | H | H | H | H | Cl | Et | 3-pyridyl | 458.9637 | 2000 |
| 22 | H | H | H | Cl | H | Et | 3-pyridyl | 458.9637 | 2000 |
| 23 | H | H | H | $CF_3$ | F | Et | 3-pyridyl | 510.5058 | 2000 |
| 24 | H | H | H | H | Cl | $CH_2CH_2N(CH_3)CH_2$-3-thiophene | Me | 521.0991 | 149 |
| 25 | Cl | H | H | H | OH | $CH_2CH_2N(CH_3)CH_2$-3-thiophene | Me | 537.0981 | 815 |
| 26 | H | H | H | $NO_2$ | H | $CH_2CH_2N(CH_3)CH_2$-3-thiophene | Me | 531.6511 | 51 |

EXAMPLE 1

Thiepino[3,2-b]pyridine-3-carboxylic Acid, 4-(2-Chlorophenyl)-1,4,6,7,8,9-hexahydro-2-phenyl-, Ethyl Ester, 5,5-Dioxide

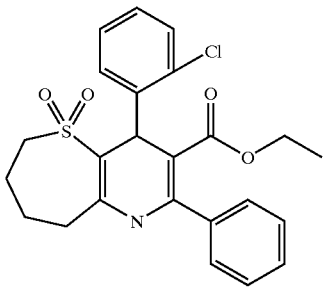

1,1-Dioxide-3-thiepanone (2.0 mmol, 0.32 g), ethyl-aminocinnamate (2.0 mmol, 0.38 g), and 2-chlorobenzaldehyde (2.0 mmol, 0.28 g) were dissolved in 10 mL of toluene and refluxed for 18 h. The mixture was concentrated to give an oil which was chrombatographed using 1:1 hexanes:ethyl acetate to give 0.092 g of product.

EXAMPLE 2

Thiepino[3,2-b]pyridine-3-carboxylic Acid, 4-(2-Chlorophenyl)-1,4,6,7,8,9-hexahydro-2-(2-thienyl)-, Ethyl Ester, 5,5-Dioxide

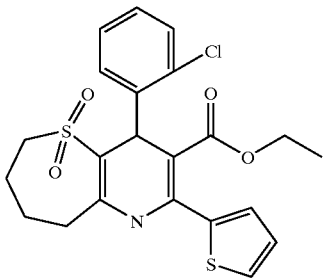

1,1-Dioxide-3-thiepanone (2.0 mmol, 0.32 g), ethyl-3-amino-3-(2-thienyl)-2-propenoate (2.0 mmol, 0.39 g), and 2-chlorobenzaldehyde (2.0 mmol, 0.28 g) were dissolved in 5 mL of dioxane and refluxed for 48 h. The mixture was concentrated to give an oil which was chromoatographed using 1:1 hexanes:ethyl acetate to give 0.118 g of product.

EXAMPLE 3

Thiepino[3,2-b]pyridine-3-carboxylic Acid, 4-(2-Chlorophenyl)-1,4,6,7,8,9-hexahydro-2-(3-pyridinyl)-, Ethyl Ester, 5,5-Dioxide

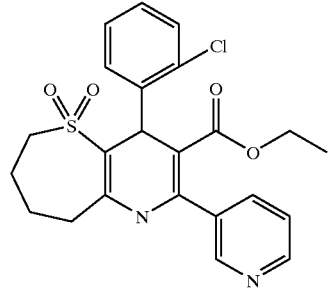

1,1-Dioxide-3-thiepanone (2.0 mmol, 0.32 g), ethyl-3-amino-3-(3-pyridyl)-2-propenoate (2.0 mmol, 0.39 g), and 2-chlorobenzaldehyde (2.0 mmol, 0.28 g) were dissolved in 5 mL of dioxane and refluxed for 48 h. The mixture was concentrated to give an oil which was chromoatographed using ethyl acetate to give 0.011 g of product.

EXAMPLE 4

Ethyl-3-amino-3-phenyl-2-[methyl(phenylmethyl)amino]-2-propenoate

Ethyl-2-[methyl(phenylmethyl)amino]-cyanoacetate (0.049 mol, 11.3 g) was dissolved in 300 mL of ether and added to 32 mL of 3M PhMgBr, and the resulting mixture was refluxed for 18 h. The reaction was cooled, quenched with sat. NH$_4$Cl solution and extracted with ether. The organics were dried, concentrated, and chromatographed using 1:1 hexanes:ethyl acetate to give 5 g of product. 1H NMR (300 MHz) CDCl$_3$: 7.6–7.2 (m, 10H), 5.01 (s, 1H), 4.27 (t, 2H), 3.59 (s, 2H), 2.73 (t, 2H), 2.31 (s, 3H).

EXAMPLE 5

Thiepino[3,2-b]pyridine-3-carboxylic Acid, 4-(2-Chlorophenyl)-1,4,6,7,8,9-hexahydro-2-phenyl-, 2-[Methyl(phenylmethyl)amino]ethyl Ester, 5,5-Dioxide

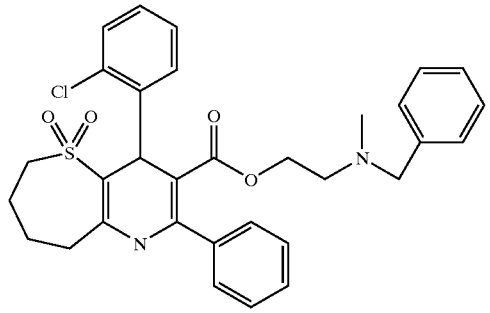

Ethyl-3-amino-3-phenyl-2-[methyl(phenylmethyl)amino]-2-propenoate (2.0 mmol, 0.62 g), 1,1-dioxide-3-thiepanone (2.0 mmol, 0.32 g), and 2-chlorobenzaldehyde (2.0 mmol, 0.28 g) were dissolved in 20 mL EtOH and refluxed for 3 h with an oil bath. The oil bath temperature was then raised to 200° C. for 1 h. The residue was cooled and chromatographed using 1:1 hexanes:ethyl acetate to give a product, which was dissolved in 5 mL of EtOAc and treated with HCl gas. The solid was filtered to give 0.025 g of product.

EXAMPLE 6

Ethyl-2-[methyl(thienylmethyl)amino]-cyanoacetate

2-[Methyl(2-thienylmethyl)amino]ethanol (0.017 mol, 3 g) and cyanoacetic acid (0.017 mol, 1.5 g) were dissolved in 200 mL of THF and DCC (0.019 mol, 3.8 g) was added. After 3 h, the resulting solid was removed and the filtrate was concentrated. The residue was passed through a six-inch silica plug using ether as solvent to give 4.0 g of product. 1H NMR (300 MHz) CDCl$_3$: 7.25 (d, 1H), 7.0–6.8 (m, 2H), 4.33 (t, 2H) 3.76 (s, 2H), 3.47 (s, 2H), 2.70 (t, 2H), 2.35 (s, 3H).

EXAMPLE 7

Ethyl-3-amino-3-phenyl-2-[methyl(thienylmethyl) amino]-2-propenoate

Ethyl-2-[methyl(thienylmethyl)amino]-cyanoacetate (0.014 mol, 3.4 g) was dissolved in 100 mL of ether and added to 9.5 mL of 3M PhMgBr, and the resulting mixture was refluxed for 18 h. The reaction was cooled, quenched with sat. NH$_4$Cl solution and extracted with ether. The organics were dried, concentrated, and chromatographed using 1:1 hexanes:ethyl acetate to give 1.4 g of product. 1H NMR (300 MHz) CDCl$_3$: 7.58 (d, 2H), 7.4 (m, 3H), 7.21 (d, 1H), 6.89 (m, 2H), 5.0 (s, 1H), 4.28 (t, 2H), 3.85 (s, 2H), 2.75 (t, 2H), 2.38 (s, 3H).

EXAMPLE 8

Thiepino[3,2-b]pyridine-3-carboxylic Acid, 4-(2-Chlorophenyl)-1,4,6,7,8,9-hexahydro-2-phenyl-, 2-[Methyl(2-thienylmethyl)amino]ethyl Ester, 5,5-Dioxide

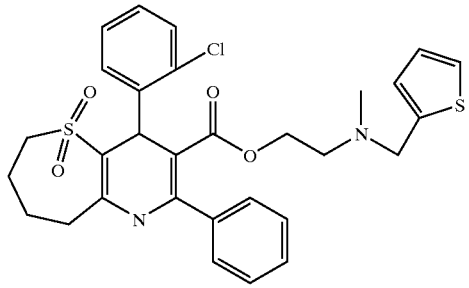

Ethyl-3-amino-3-phenyl-2-[methyl(thienylmethyl) amino]-2-propenoate (0.63 mmol, 0.20 g), 1,1-dioxide-3-thiepanone (0.63 mmol, 0.10 g), and 2-chlorobenzaldehyde (0.63 mmol, 0.089 g) were dissolved in 5 mL of dioxane and refluxed for 48 h. The reaction was concentrated and chromatographed using 1:1 hexanes:ethyl acetate to give 0.082 g of product.

EXAMPLE 9

Thiepino[3,2-b]pyridine-3-carboxylic Acid, 4-(2-Chlorophenyl)-1,4,6,7,8,9-hexahydro-2-methyl-, 2-[Methyl(2-thienylmethyl)amino]ethyl Ester, 5,5-Dioxide

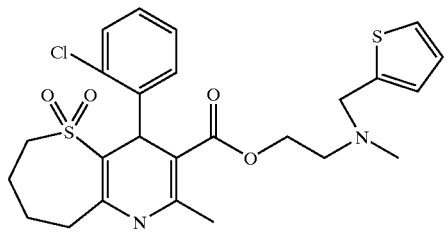

Ethyl-2-[methyl(2-thienylmethyl)amino]-3-oxo-butanoate (1.7 mmol, 0.42 g), 1,1-dioxide-3-thiepanone (1.7 mmol, 0.28 g), ammonium acetate (3.4 mmol, 0.26 g), and 2-chlorobenzaldehyde (1.7 mmol, 0.24 g) were dissolved in 20 mL of IPA and refluxed for 18 h. The reaction was concentrated and chromatographed using 1:1 hexanes:ethyl acetate to give 0.26 g of product.

EXAMPLE 10

2-[Methyl(3-thienylmethyl)amino]ethanol 2-(Methylamino)-ethanol (0.047 mol, 3.5 g) and 3-thiophenecarboxaldehyde (0.047 mol, 5.3 g) were dissolved in 50 mL of MeOH and 10 mL of AcOH. NaCNBH$_3$ (0.023 mol, 1.5 g) was added portionwise, and the resulting mixture was stirred for 18 h. The solvent was removed in vacuo, and the residue was taken up in 1N KOH and extracted with EtOAc. The organics were dried and concentrated to give an oil which was filtered through a six inch silica gel plug using 1:1 hexanes:ethyl acetate to give 7.6 g of product. 1H NMR (300 MHz) CDCl$_3$: 7.3 (m, 1H), 7.12 (s, 1H), 7.05 (d, 1H), 3.6 (m, 4H), 2.57 (t, 2H), 2.25 (s, 3H).

EXAMPLE 11

Ethyl-2-[methyl(3-thienylmethyl)amino]-3-oxo-butanoate

2-[Methyl(3-thienylmethyl)amino]ethanol (0.044 mol, 7.6 g) and diketene (0.044 mol, 3.7 g) were dissolved in 20 mL of CHCl$_3$. A catalytic amount of Et$_3$N was added and the mixture was stirred for 18 h. Concentration gives 11.2 g of product. 1H NMR (300 MHz) CDCl$_3$: 7.26 (m, 1H), 7.10 (s, 1H), 7.05 (d, 1H), 4.27 (t, 2H), 3.60 (s,2H), 3.48 (s, 2H), 2.66 (t, 2H), 2.28 (s, 3H), 2.27 (s, 3H).

EXAMPLE 12

Thiepino[3,2-b]pyridine-3-carboxylic Acid, 4-(2-Chlorophenyl)-1,4,6,7,8,9-hexahydro-2-methyl-, 2-[Methyl(3-thienylmethyl)amino]ethyl Ester, 5,5-Dioxide

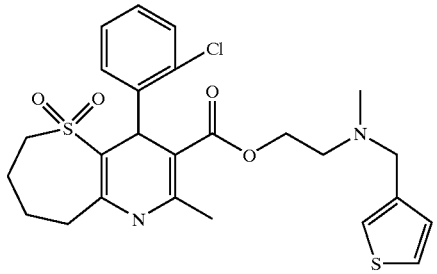

Ethyl-2-[methyl(3-thienylmethyl)amino]-3-oxo-butanoate (1.7 mmol, 0.42 g), 1,1-dioxide-3-thiepanone (1.7 mmol, 0.28 g), ammonium acetate (3.4 mmol, 0.26 g), and 2-chlorobenzaldehyde (1.7 mmol, 0.24 g) were dissolved in 20 mL of IPA and refluxed for 18 h. The reaction was concentrated and chromatographed using 1:1 hexanes:ethyl acetate to give 0.066 g of product.

B. Assays

EXAMPLE 13

Assay for Inhibition of Nitrendpine Binding

Female, New Zealand white rabbits (1–2 kg) are sacrificed by cervical dislocation, and the heart is immediately removed, cleaned and chopped into small pieces. The tissue is homogenized in 5×times volume of 0.05M Hepes buffer, pH 7.4. The homogenate is centrifuged at 4000 g for 10 minutes, and the supernatant is re-centrifuged at 42,000×g for 90 minutes. The resulting membrane pellet is re-suspended (0.7 ml/g weight) in 0.05M Hepes, pH 7.4 and stored at 70° C. until used. Each tube of the binding assay contains $^3$H-nitrendipine (0.05–0.50 nM), buffer, membranes (0.10 ml), and test compound in a total volume of 1.0 ml. After 90 minutes at 4° C., the bound nitrendipine is separated from the unbound by filtration on Whatman GF/C filters. After rinsing, the filters are dried and counted in a liquid scintillation counter.

Non-specific binding of $^3$H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be calculated.

EXAMPLE 14

Test for Inhibition of Calcium-Dependent Smooth Muscle Contraction

The trachea and the aorta from dogs sacrificed by excess KCl injection are stored overnight at 4° C. in oxygenated Krebs-Henseleit buffer. Tracheal rings, one cartilage segment wide (5–10 mm), are cut starting from the bronchial end. Rings of aorta tissue of the same width are also prepared. After cutting the cartilage, the trachealis muscle tissue and the aorta tissue are suspended in oxygenated Krebs-Henseleit buffer at 37° C. in a 25 ml tissue bath. After a 60-minute equilibration period, the tissues are challenged with 10 μM carbachol. After 5 minutes, the tissues are rinsed and allowed to rest 50 minutes. The tissues are then challenged with 50 mM KCl and, after 30 minutes, the contractions are quantitated. The tissues are then rinsed and re-equilibrated for 50 minutes. Test compounds are then added for 10 minutes, and the tissue is re-challenged with 50 mM KCl. After 30 minutes, the contraction is recorded. A percent inhibition of smooth muscle contraction can then be calculated.

What is claimed is:

1. A compound of Formula I,

Formula I

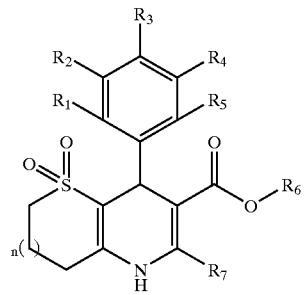

or a pharmaceutically acceptable salt thereof, wherein (a) $R_1$, $R_2$, $R_3$, $R_4$ and $R_5$ are independently selected from H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);

(b) $R_6$ is selected from H, $C_{1-5}$ straight or branched alkyl, substituted alkyl, aryl, 3-piperidyl, N-substituted 3-piperidyl, and N-substituted 2-pyrrolidinyl methylene, wherein
said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
(i) R' and R" are independently selected from the group consisting of H, $C_{1-8}$ straight or branched alkyl, $C_{3-7}$ cycloalkyl, phenyl, benzyl, and phenethyl, or (ii) R' and R" together form a heterocyclic ring selected from the group consisting of piperidino, pyrrolidino, morpholino, thiomorpholino, piperazino, 2-thieno, 3-thieno, and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl);

(c) $R_7$ is selected from aryl, 3-pyridyl, 2-thieno, and 3-thieno; and (d) n is an integer from 1 to 5.

2. The compound of claim 1 wherein $R_6$ is alkyl.

3. The compound of claim 1 wherein $R_7$ is selected from phenyl, 2-thieno, and 3-pyridyl.

4. The compound of claim 1 wherein $R_1$, $R_2$, $R_3$, $R_4$ and $R_5$ are independently selected from H, OH, halogen, $NO_2$, and trifluoromethyl.

5. The compound of claim 1 which is thiepino[3,2-b]pyridine-3-carboxylic acid, 4-(4-chlorophenyl)-1,4,6,7,8,9-hexahydro-2-phenyl-, ethyl ester, 5,5-dioxide.

6. The compound of claim 1 which is thiepino[3,2-b]pyridine-3-carboxylic acid, 4-(2,3-dichlorophenyl)-1,4,6,7,8,9-hexahydro-2-phenyl-, ethyl ester, 5,5-dioxide.

7. The compound of claim 1 which is thiepino[3,2-b]pyridine-3-carboxylic acid, 4-(3-chlorophenyl)-1,4,6,7,8,9-hexahydro-2-phenyl-, methyl ester, 5,5-dioxide.

8. The compound of claim 1 which is thiepino[3,2-b]pyridine-3-carboxylic acid, 4-(2-chloro-6-hydroxyphenyl)-1,4,6,7,8,9-hexahydro-2-phenyl-, ethyl ester, 5,5-dioxide.

9. The compound of claim 1 which is thiepino[3,2-b]pyridine-3-carboxylic acid, 4-(2-chlorophenyl)-1,4,6,7,8,9-hexahydro-2-phenyl-, ethyl ester, 5,5-dioxide.

10. The compound of claim 1 which is thiepino[3,2-b]pyridine-3-carboxylic acid, 1,4,6,7,8,9-hexahydro-4-(2,3,4,5,6-pentafluorophenyl)-2-phenyl-, ethyl ester, 5,5-dioxide.

11. The compound of claim 1 which is thiepino[3,2-b]pyridine-3-carboxylic acid, 1,4,6,7,8,9-hexahydro-4-(3-nitrophenyl)-2-phenyl-, ethyl ester, 5,5-dioxide.

12. The compound of claim 1 which is thiepino[3,2-b]pyridine-3-carboxylic acid, 4-(2-chlorophenyl)-1,4,6,7,8,9-hexahydro-2-(2-thienyl)-, ethyl ester, 5,5-dioxide.

13. The compound of claim 1 which is thiepino[3,2-b]pyridine-3-carboxylic acid, 4-(3-chlorophenyl)-1,4,6,7,8,9-hexahydro-2-(2-thienyl)-, ethyl ester, 5,5-dioxide.

14. The compound of claim 1 which is thiepino[3,2-b]pyridine-3-carboxylic acid, 1,4,6,7,8,9-hexahydro-4-(3-nitrophenyl)-2-(2-thienyl)-, ethyl ester, 5,5-dioxide.

15. The compound of claim 1 which is thiepino[3,2-b]pyridine-3-carboxylic acid, 4-(2-chlorophenyl)-1,4,6,7,8,9-hexahydro-2-(3-pyridinyl)-, ethyl ester, 5,5-dioxide.

16. The compound of claim 1 which is thiepino[3,2-b]pyridine-3-carboxylic acid, 4-(3-chlorophenyl)-1,4,6,7,8,9-hexahydro-2-(3-pyridinyl)-, ethyl ester, 5,5-dioxide.

17. The compound of claim 1 which is thiepino[3,2-b]pyridine-3-carboxylic acid, 4-[2-fluoro-3-(trifluoromethyl)phenyl]-1,4,6,7,8,9-hexahydro-2-(3-pyridinyl)-, ethyl ester, 5,5-dioxide.

18. A compound of Formula II,

Formula II or a pharmaceutically acceptable salt thereof, wherein
(a) $R_1$, $R_2$, $R_3$, $R_4$ and $R_5$ are independently selected from H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) $R_8$ is —$(CH_2)_p$(heterocyclyl);
(c) $R_9$ is selected from H, alkyl, cycloalkyl, aryl, and arylalkyl;
(d) $R_{10}$ is selected from H, amino, alkyl, aryl, trifluoromethyl, and alkoxymethyl; and
(e) m, n, and p are each an integer from 1 to 5.

19. The compound of claim 18 wherein $R_{10}$ is alkyl or aryl.

20. The compound of claim 19 wherein $R_{10}$ is methyl or phenyl.

21. The compound of claim 18 wherein $R_9$ is alkyl.

22. The compound of claim 18 wherein $R_8$ is selected from —$CH_2$-2-thiophene and —$CH_2$-3-thiophene.

23. The compound of claim 18 wherein $R_1$, $R_2$, $R_3$, $R_4$ and $R_5$ are independently selected from OH, halogen, cyano, and $NO_2$.

24. The compound of claim 18 which is thiepino[3,2-b]pyridine-3-carboxylic acid, 4-(2-chloro-6-fluorophenyl)-1,4,6,7,8,9-hexahydro-2-methyl-, 2-[methyl(2-thienylmethyl)amino]ethyl ester, 5,5-dioxide.

25. The compound of claim 18 which is thiepino[3,2-b]pyridine-3-carboxylic acid, 1,4,6,7,8,9-hexahydro-2-methyl-4-(2,3,4,5,6-pentafluorophenyl)-, 2-[methyl(2-thienylmethyl)amino]ethyl ester, 5,5-dioxide.

26. The compound of claim 18 which is thiepino[3,2-b]pyridine-3-carboxylic acid, 1,4,6,7,8,9-hexahydro-2-methyl-4-(3-nitrophenyl)-, 2-[methyl(2-thienylmethyl)amino]ethyl ester, 5,5-dioxide.

27. The compound of claim 18 which is thiepino[3,2-b]pyridine-3-carboxylic acid, 4-(2-chlorophenyl)-1,4,6,7,8,9-hexahydro-2-methyl-, 2-[methyl(2-thienylmethyl)amino]ethyl ester, 5,5-dioxide.

28. The compound of claim 18 which is thiepino[3,2-b]pyridine-3-10 carboxylic acid, 4-(2-chlorophenyl)-1,4,6,7,8,9-hexahydro-2-phenyl-, 2-[methyl(2-thienylmethyl)amino]ethyl ester, 5,5-dioxide.

29. The compound of claim 18 which is thiepino[3,2-b]pyridine-3-carboxylic acid, 1,4,6,7,8,9-hexahydro-4-(3-nitrophenyl)-2-phenyl-, 2-[methyl(2-thienylmethyl)amino]ethyl ester, 5,5-dioxide.

30. The compound of claim 18 which is thiepino[3,2-b]pyridine-3-carboxylic acid, 4-(3-chlorophenyl)-1,4,6,7,8,9-hexahydro-2-phenyl-, 2-[methyl(2-thienylmethyl)amino]ethyl ester, 5,5-dioxide.

31. The compound of claim 18 which is thiepino[3,2-b]pyridine-3-carboxylic acid, 4-(2-chlorophenyl)-1,4,6,7,8,9-hexahydro-2-methyl-, 2-[methyl(3-thienylmethyl)amino]ethyl ester, 5,5-dioxide.

32. The compound of claim 18 which is thiepino[3,2-b]pyridine-3-carboxylic acid, 4-(2-chloro-6-hydroxyphenyl)-1,4,6,7,8,9-hexahydro-2-methyl-, 2-[methyl(3-thienylmethyl)amino]ethyl ester, 5,5-dioxide.

33. The compound of claim 18 which is thiepino[3,2-b]pyridine-3-carboxylic acid, 1,4,6,7,8,9-hexahydro-2-methyl-4-(3-nitrophenyl)-, 2-[methyl(3-thienylmethyl)amino]ethyl ester, 5,5-dioxide.

34. A compound of Formula V,

Formula V or a pharmaceutically acceptable salt thereof, wherein
(a) $R_1$, $R_2$, $R_3$, $R_4$ and $R_5$ are independently selected from H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);

(b) X is $R_7$ or $R_{10}$ wherein
$R_7$ is selected from aryl, 3-pyridyl, 2-thieno, and 3-thieno; and
$R_{10}$ is selected from H, amino, alkyl, aryl, trifluoromethyl, and alkoxymethyl;

(c) $R_{11}$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-OC(O)R''', -alkyl-C(O) R''', -alkyl-C(O)OR''', -alkyl-N(R'')C(O)R''', and -alkyl-N(R''')C(O)OR''', wherein
R''' and R'''' are independently selected from the group consisting of hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl); and (d) n is an integer from 1 to 5.

35. The compound of claim 34 wherein $R_7$ is methyl and $R_1$, $R_2$, $R_3$, $R_4$, and $R_5$ are independently selected from hydrogen, halogen, trifluoromethyl and $NO_2$.

36. The compound of claim 34 wherein $R_1$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-C(O)R''', -alkyl-N(R'')C(O)R''', and -alkyl-N(R''')C(O)OR'''.

37. The compound of claim 34 wherein $R_{11}$ is selected from the group consisting of —$(CH_2)_2OC(O)CH(CH_2CH_3)_2$, —$(CH_2)_2OC(O)CH(CH_3)_2$, —$(CH_2)_2OC(O)PH$—$OCH(CH_3)_2$, —$CH_2OC(O)CH_2N(CH_3)CH_2PH$, —$CH_2OC(O)CH_2$—$PH$—$N(CH_3)_2$, and —$CH_2OC(O)CH(CH_2)_6$.

38. A pharmaceutical composition comprising the compound of claim 1, 18, or 34 and a pharmaceutically acceptable carrier.

39. A method of treating a subject suffering from a disorder selected from the group consisting of hypersensitivity, allergy, asthma. bronchospasm, dysmenorrhea, esophageal spasm, glaucoma, premature labor, a urinary tract disorder, a gastrointestinal disorder and a cardiovascular disorder selected from the group consisting of hypertension, ischemia, angina, congestive heart failure, myocardial infarction and stroke, which method comprises administering to the subject a therapeutically effective dose of the pharmaceutical composition of claim 38.

40. The method of claim 39, wherein the disorder is asthma.

41. The method of claim 39, wherein the cardiovascular disorder is selected from the group consisting of hypertension, ischemia, angina, congestive heart failure, myocardial infarction and stroke.

42. A method of inhibiting in a subject the onset of a disorder selected from the group consisting of hypersensitivity, allergy, asthma. bronchospasm, dysmenorrhea, esophageal spasm, glaucoma, premature labor, a urinary tract disorder, a gastrointestinal disorder and a cardiovascular disorder selected from the group consisting of hypertension, ischemia, angina, congestive heart failure, myocardial infarction and stroke which method comprises administering to the subject a prophylactically effective dose of the pharmaceutical composition of claim 38.

43. The method of claim 42, wherein the disorder is asthma.

44. The method of claim 42, wherein the cardiovascular disorder is selected from the group consisting of hypertension, ischemia, angina, congestive heart failure, myocardial infarction and stroke.

45. A process for preparing the compound of claim 1 or 18 having the structure shown as Formula III,

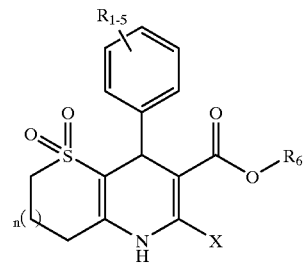

III wherein X is $R_7$ or $R_{10}$, which process comprises the steps of:

a) reacting a compound of Formula 1a with $HOR_6$ to form a compound of Formula 1b;

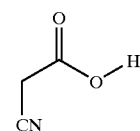

1a

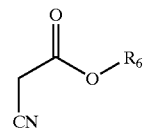

1b

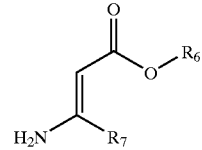

1c b) reacting the compound of Formula 1b with $R_7MgBr$ to form a compound of Formula 1c; and

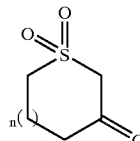

1d

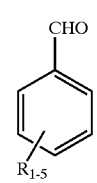

1e

-continued

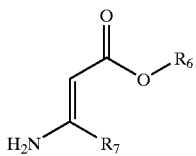

1c c) reacting a compound of Formula 1d and a compound of Formula 1e with the compound of Formula 1c to form a compound of Formula III.

46. A process for preparing the compound of claim 1 or 18 having the structure shown as Formula III,

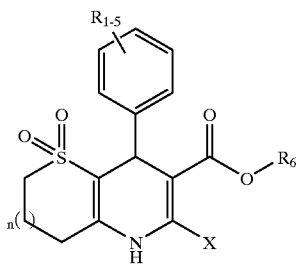

III wherein X is $R_7$ or $R_{10}$, which process comprises the step of reacting a compound of Formula 1d and a compound of Formula 1e with the compound of Formula 1f to form a compound of Formula III.

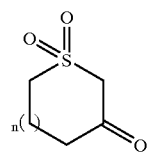

1d

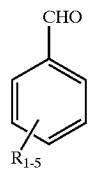

1e

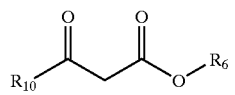

1f

* * * * *